United States Patent
Kimball et al.

(10) Patent No.: US 10,010,457 B2
(45) Date of Patent: Jul. 3, 2018

(54) TAMPON WITH PENETRATING GROOVE SEGMENTS

(71) Applicant: JOHNSON & JOHNSON GMBH, Neuss (DE)

(72) Inventors: David L. Kimball, Flemington, NJ (US); Tony C. Ng, East Brunswick, NJ (US); Tara Zedayko, Hillsborough, NJ (US)

(73) Assignee: Johnson & Johnson GmbH (DE)

( * ) Notice: Subject to any disclaimer, the term of this patent is extended or adjusted under 35 U.S.C. 154(b) by 387 days.

(21) Appl. No.: 14/877,012

(22) Filed: Oct. 7, 2015

(65) Prior Publication Data

US 2016/0022508 A1 Jan. 28, 2016

Related U.S. Application Data

(62) Division of application No. 13/717,919, filed on Dec. 18, 2012, now Pat. No. 9,168,184.

(51) Int. Cl.
*A61F 13/20* (2006.01)

(52) U.S. Cl.
CPC ...... *A61F 13/2034* (2013.01); *A61F 13/2088* (2013.01); *A61F 13/2091* (2013.01); *A61F 13/2037* (2013.01); *A61F 13/2051* (2013.01); *A61F 13/2077* (2013.01)

(58) Field of Classification Search
CPC .............. A61F 13/2082; A61F 13/2088; A61F 13/2091; A61F 13/2085; A61F 13/2034; A61F 13/15707; A61F 13/2054; A61F 13/2037; A61F 13/2051; B30B 5/00; B30B 7/00; B30B 7/04; B30B 15/02; B30B 15/026; B30B 9/00; B30B 9/28
USPC ........................................... 28/118, 119, 121
See application file for complete search history.

(56) References Cited

U.S. PATENT DOCUMENTS

| | | | | |
|---|---|---|---|---|
| 2,263,909 A | * | 11/1941 | Webb | A61F 13/2051 28/120 |
| 2,425,004 A | * | 8/1947 | Rabell | A61F 13/2085 264/258 |
| 2,798,260 A | | 7/1957 | Friedrich et al. | |
| 3,422,496 A | | 1/1969 | Wolff et al. | |
| 3,596,328 A | | 8/1971 | Voss | |
| 3,683,915 A | | 8/1972 | Voss | |

(Continued)

FOREIGN PATENT DOCUMENTS

| | | |
|---|---|---|
| DE | 40502965-0001 | 10/2005 |
| DE | 40502965-0002 | 10/2005 |

(Continued)

OTHER PUBLICATIONS

European Search Report dated Jan. 20, 2017, Application No. EP16183462.

(Continued)

*Primary Examiner* — Amy Vanatta

(57) ABSTRACT

The present invention relates to an intravaginal tampon for feminine hygiene. In particular, it relates to methods for producing such a tampon having relatively deep, penetrating grooves in which adjacent penetrating jaws pass through the same tampon press space during manufacture and to an apparatus useful in making such a tampon as well as the tampons made therewith.

8 Claims, 16 Drawing Sheets

(56) References Cited

U.S. PATENT DOCUMENTS

| | | | |
|---|---|---|---|
| 4,109,354 A * | 8/1978 | Ronc | A61F 13/2085 28/119 |
| 4,816,100 A | 3/1989 | Friese | |
| 4,951,368 A * | 8/1990 | Heinen | A61F 13/2085 28/118 |
| 5,458,835 A | 10/1995 | Wilkes et al. | |
| 5,592,725 A * | 1/1997 | Brinker | A61F 13/206 28/118 |
| 5,813,102 A | 9/1998 | Leutwyler et al. | |
| 5,909,884 A | 6/1999 | Schwankhart | |
| 6,310,269 B1 * | 10/2001 | Friese | A61F 13/2051 28/118 |
| 7,311,699 B2 | 12/2007 | Carlin | |
| 7,549,982 B2 | 6/2009 | Carlin | |
| 7,845,055 B1 | 12/2010 | Kimball et al. | |
| 8,029,485 B2 | 10/2011 | Jensen | |
| 8,153,582 B2 | 4/2012 | Carlucci | |
| 8,574,210 B2 | 11/2013 | Van Ingelgem et al. | |
| 8,747,378 B2 | 6/2014 | Van Ingelgem et al. | |
| 2002/0151859 A1 | 10/2002 | Schoelling | |
| 2005/0193536 A1 * | 9/2005 | Ingelgem | A61F 13/206 28/118 |
| 2007/0083182 A1 | 4/2007 | Schoelling | |
| 2009/0024103 A1 | 1/2009 | Van Ingelgem et al. | |
| 2011/0092940 A1 | 4/2011 | Fung et al. | |
| 2012/0010587 A1 | 1/2012 | Smet | |
| 2012/0089111 A1 | 4/2012 | Magnusson et al. | |
| 2012/0137479 A1 * | 6/2012 | Rolli | A61F 13/2085 28/118 |
| 2012/0187600 A1 * | 7/2012 | Graber | A61F 13/2085 264/320 |
| 2013/0110074 A1 * | 5/2013 | Smet | A61F 13/2051 604/385.17 |
| 2014/0090218 A1 * | 4/2014 | Gehling | A61F 13/2088 28/118 |
| 2014/0090219 A1 * | 4/2014 | Gehling | A61F 13/2088 28/118 |
| 2014/0093604 A1 * | 4/2014 | Gehling | B29C 43/021 425/340 |

FOREIGN PATENT DOCUMENTS

| | | |
|---|---|---|
| DE | 40502965-0003 | 10/2005 |
| DE | 40502965-0004 | 10/2005 |
| DE | 40502965-0005 | 10/2005 |
| DE | 40502965-0006 | 10/2005 |
| DE | 40502965-0007 | 10/2005 |
| DE | 40502965-0008 | 10/2005 |
| DE | 40502965-0009 | 10/2005 |
| DE | 40502965-0010 | 10/2005 |
| EP | 422660 | 4/1991 |
| EP | 611562 | 8/1994 |
| EP | 1459720 | 2/2004 |
| EP | 1481656 | 12/2004 |
| EP | 1547555 | 6/2005 |
| EP | 1683503 | 7/2006 |
| EP | 1983953 | 10/2008 |
| WO | WO 2007/088057 | 8/2007 |
| WO | WO 2008/095937 | 4/2008 |
| WO | WO 2008/135925 A1 | 11/2008 |
| WO | WO 2009/129910 | 10/2009 |
| WO | WO 2010/144061 | 12/2010 |
| WO | WO 2011/000507 | 1/2011 |
| WO | WO 2011/002357 | 1/2011 |
| WO | WO 2010/069908 A | 1/2012 |
| WO | WO 2012/004315 | 1/2012 |

OTHER PUBLICATIONS

Australian communicated dated Feb. 15, 2017, Application No. AU2013231154.

Japan Application No. JP 2013-199478 dated Aug. 10, 2017.

Australian communication dated Feb. 15, 2017, Application No. AU2013231154.

* cited by examiner

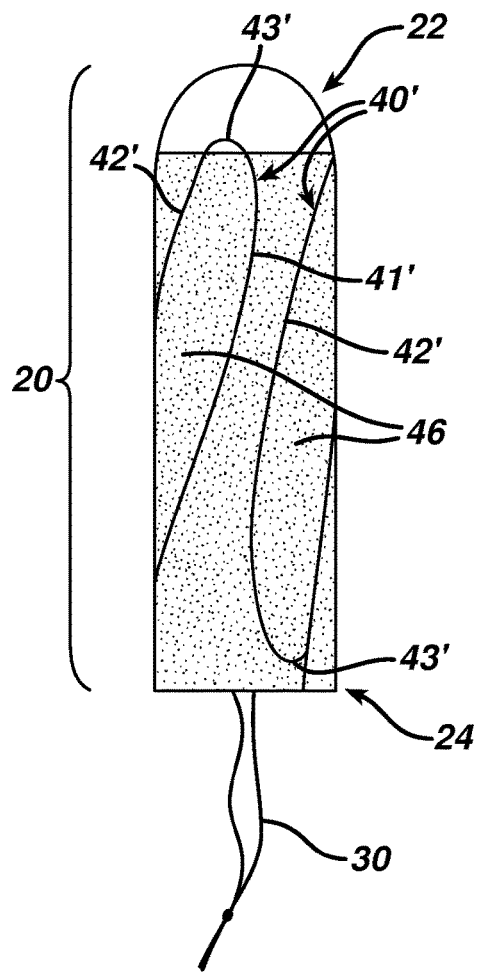
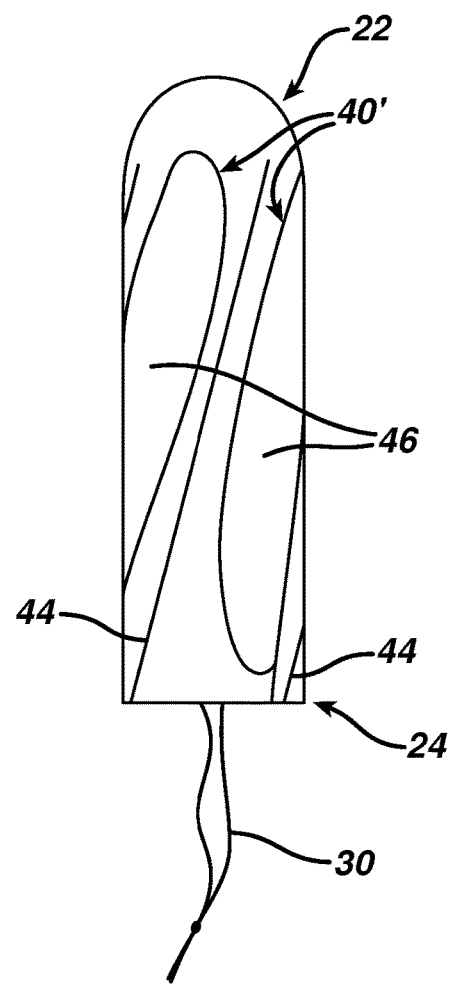
FIG. 5    FIG. 6

TAMPON WITH PENETRATING GROOVE SEGMENTS

CROSS-REFERENCE TO RELATED APPLICATIONS

This application is a divisional of U.S. application Ser. No. 13/717,919 filed Dec. 18, 2012 which claims the benefit of U.S. provisional application 61/706,346 filed on Sep. 27, 2012. The complete disclosures of which are hereby incorporated herein by reference of all purposes.

FIELD OF THE INVENTION

The present invention relates to an intravaginal tampon for feminine hygiene. In particular, it relates to methods for producing such a tampon having relatively deep, penetrating grooves in which adjacent penetrating jaws pass through the same tampon press space during manufacture and to an apparatus useful in making such a tampon as well as the tampons made therewith.

BACKGROUND OF THE INVENTION

Devices for intravaginally capturing and storing bodily fluid are commercially available and known in the literature. Intravaginal tampons for feminine hygiene are the most common example of such devices. Commercially available tampons are generally compressed cylindrical masses of absorbent fibers that may be contained by an absorbent or nonabsorbent cover layer.

The tampon is inserted into the human vagina and retained there for a time for the purpose of capturing and storing intravaginal bodily fluids, most commonly menstrual fluid. As intravaginal bodily fluid contacts the tampon, it should be absorbed and retained by the absorbent material of the tampon. After a time, the tampon and its retained fluid is removed and disposed, and if necessary, another tampon is inserted.

A drawback often encountered with commercially available tampons is the tendency toward premature failure, which may be defined as bodily fluid leakage from the vagina while the tampon is in place and before the tampon is completely saturated with the bodily fluid. The patent art typically describes a problem believed to occur that an unexpanded, compressed tampon is unable to immediately absorb fluid. Therefore, it presumes that premature leakage may occur when bodily fluid contacts a portion of the compressed tampon, and the fluid is not readily absorbed.

One way to prevent premature leakage from occurring is to provide designed pathways for fluid moving along the outer tampon surface. While this increase to the pathways may improve the fluid absorption, adding grooves during the manufacturing process can raise process issues. The prior art is replete with examples of attempts to incorporate grooves into tampons. Often new steps are added to an already complicated manufacturing process or the process is not fully described.

Friese et al., EP 0422660 B2, discloses an apparatus for producing a tampon with longitudinal grooves. The apparatus for making the tampon includes two groups of dies arranged in a plane perpendicular to the press axis. The first group of dies form press segments and the second group of dies form sliding plates. Each of the dies has press cutters projecting from the faces. The blank is pressed into a preform having a core with high compression and longitudinal ribs separated by grooves. The dies do not include a surface for forming shoulders.

Schoelling, US 2002-0151859 A1, discloses an apparatus for producing tampons having spirally shaped, pressed longitudinal grooves. The apparatus has press jaws of substantially equal dimensions which are arranged in a star formation with respect to the press axis. The jaws can be moved synchronously between open and closed positions. Each press jaw has a stepped pressing surface including a pressing blade and a pressing shoulder. The area of the pressing shoulder is great than the area of the pressing blade. The pressing blade and pressing shoulder can extend over a circumferential angle α of between 80 to 150° in the closed or pressing position. The press jaws are slightly retracted to give clearance when the preform is ejected from the press.

Van Ingelgem et al., EP 1547555 B1 purports to disclose an apparatus for manufacturing tampons with at least three press jaws, each press jaw having a penetrating segment for penetrating the absorbent material and pressing shoulder. The median of the penetrating segment diverges from the radius of that penetrating segment when in the press. The median of the penetrating segment is the straight line drawn in a cross section of the penetrating segment, through its tip and the midpoint of its base. One press jaw may comprise either a penetrating segment or a pressing shoulder, or a combination of one penetrating segment and pressing shoulders arranged at either or both sides of the penetrating segment. If the penetrating segment and pressing shoulders are fixed to separate press jaws, it is preferably that they press simultaneously. The press jaws, in particular, the penetrating segments can have a straight, sinusoidal, spiral or helical shape in the longitudinal direction to form essentially straight, sinusoidal, spiral, or helical grooves in the axial direction of the tampon. The resultant tampon has at least three ribs, in transverse cross-section, has a median at least partially diverging from the radius where the median of the rib is the line drawn through the midpoint of a series of arc lines, bound by the edges of the rib, wherein the arcs have a common center which is the midpoint of the X-X cross-section of the tampon.

Schmidt, EP 1459720 B1, purports to disclose increasing the surface area of a tampon by utilizing grooves that are formed in a wave shape. While multiple examples are shown, including wavy grooves with angled points, this publication does not disclose specifics on how to manufacture the tampons. In particular, the publication does not include specifics about compression, the press jaws or how the preform or tampon is ejected from the press.

Ruhlmann, WO 2009/129910 A1, purports to disclose a tampon having at least one first surface groove and at least one second surface groove that crosses the first surface groove along their path between a proximal end and a distal end of the tampon. However, the disclosure fails to teach how the crossing grooves are formed, especially in a commercially-feasible manufacturing process and/or with a cover.

Fung, US 2011-0092940 A1, discloses an intravaginal tampon formed of compressed material and has an outer surface with at least two segmented grooves are formed therein, and each segmented groove is separated from and spaced at a distance from an adjacent segmented groove. Each segmented groove has at least one substantially longitudinal segment and at least one accumulator segment. The arrangement of the segments provides a pooling region to impede bodily fluid flow along the outer surface of the tampon.

While the above examples describe tampons with grooves or the process for making such tampon, these tampons do not have visually distinct zones with different bodily fluid handling characteristics. In addition, the processes do not show how to make such a unique intravaginal tampon.

Further, the above examples fail to provide a tampon having intersecting longitudinal groove segments that penetrate deeply to provide fluid access into the absorbent structure and to provide column strength. Such penetrating grooves also provide a place into which to tuck or fold excess liquid permeable cover material resulting from tampon blank compression with a generally (non-stretchy) coverstock.

SUMMARY OF THE INVENTION

It has been discovered that intersecting groove segments can form deeply penetrating grooves in substantially cylindrical tampons to provide the benefits of deep grooves to transfer fluid into the tampon core and the benefits of intersecting grooves on the surface of the tampon.

In one aspect of the invention, a process of forming a compressed tampon pledget having substantially longitudinal grooves and a predetermined finished diameter includes inserting a tampon blank substantially enclosed in a liquid permeable cover into a press cavity, performing an initial compression step by moving into the press cavity toward the central press axis a plurality of longitudinal penetrating dies having pressing faces, backing the penetrating dies away from the central press axis, performing a second compression step, transferring the compressed tampon pledget to a cylindrical carrier having an internal diameter less than the predetermined finished diameter, and enclosing the compressed tampon pledget in a primary package having an internal diameter substantially equal to predetermined finished diameter thereby allowing the compressed tampon pledget to expand to the predetermined finished diameter. The press cavity has a central press axis and a plurality of elongate press dies disposed about the central press axis, wherein the tampon blank has a longitudinal axis that is disposed substantially along the central press axis. The pressing faces of the penetrating dies correspond to a plurality of longitudinal groove segments in the desired compressed tampon pledget, and at least one first penetrating die has a pressing face corresponding to a desired first groove segment shape and at least one second penetrating die has a pressing face corresponding to a second groove segment shape. The initial compression step produces a preform that has a plurality of substantially longitudinal grooves interspaced with a plurality of substantially longitudinal ribs. The first and second groove segment shapes combine to provide a groove form on the outer surface of the compressed tampon pledget, wherein the groove form has an intersection proximate to one end of the compressed tampon pledget. The pressing faces of the first and second penetrating dies are positioned at a closed position having a clear distance from the central press axis that is less than the predetermined finished diameter in the initial compression step. The pressing face of the first penetrating die extends longitudinally beyond the pressing face of the second penetrating die toward the end of the compressed tampon pledget whereby the first and second penetrating die pass through the same space within the press to form the groove form. The second compression step includes applying to the substantially longitudinal ribs of the preform a radial pressure directed toward the central press axis to provide a compressed tampon pledget of reduced diameter relative to the preform.

In another aspect, the present invention relates to an intravaginal tampon for feminine hygiene including a generally cylindrical absorbent pledget and a withdrawal element operatively connected to the generally cylindrical pledget proximate to the withdrawal end thereof. The absorbent pledget has a length, a longitudinal axis, an insertion end, and a withdrawal end. It includes a mass of fibers compressed into a self sustaining shape and a sheet-like fluid-permeable cover substantially enclosing the mass of fibers. The absorbent pledget has at least one groove form on the outer surface of the compressed tampon pledget, wherein the groove form has a turn comprising an intersection of at least two groove segments having a depth of at least about 0.7 mm proximate to one end of the compressed tampon pledget.

In yet another aspect, the present invention relates to an apparatus for manufacturing an intravaginal tampon for feminine hygiene. The apparatus includes a tampon press, a cylindrical carrier, and means to enclose the compressed tampon pledget in a primary package having an internal diameter substantially equal to a predetermined finished diameter. The press has a central press axis and it includes a plurality of elongate press dies disposed about central press axis to form a press cavity. The elongate press dies include a plurality of longitudinal penetrating dies having pressing faces corresponding to a plurality of longitudinal groove segments in a desired compressed tampon pledget. At least one of the press dies is a first penetrating die having a pressing shape corresponding to a desired first groove segment shape and at least one other of the press dies is a second penetrating die having a pressing face corresponding to a second groove segment shape. The first groove segment shape and the second groove segment shape combine to form a groove form on a tampon formed in the press. In addition, the pressing face of the first penetrating die extends longitudinally beyond the pressing face of the second penetrating die toward an end of the of the press cavity. Thus, the first and second penetrating dies are capable of passing through the same space within the press to form the groove form. The press also includes a control mechanism to control movement of the elongate press dies into and out of the press cavity.

Other aspects and features of the present invention will become apparent in those ordinarily skilled in the art upon review of the following description of specific embodiments of the invention in conjunction with the accompanying drawings.

BRIEF DESCRIPTION OF THE DRAWING

FIG. 5 is a side view of a fifth embodiment of a tampon according to the present invention.

FIG. 6 is a side view of a sixth embodiment of a tampon according to the present invention.

DETAILED DESCRIPTION OF THE PREFERRED EMBODIMENTS

Figure 1:
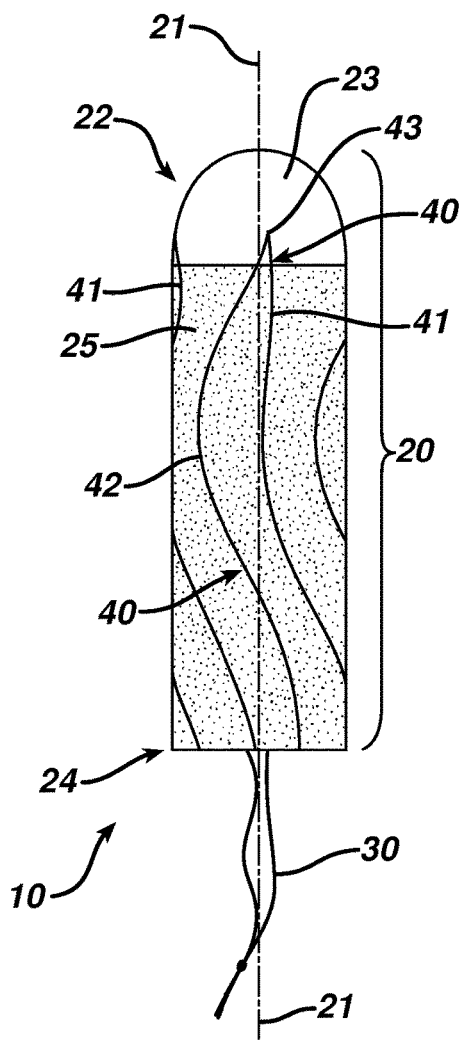
FIG. 1 is a side view of one embodiment of a tampon according to the present invention.

As used herein the specification and the claims, the term "groove" and variants thereof relate to an indention into the surface of the tampon. For clarification, grooves may be "penetrating grooves", extending at least 0.7 mm (or 10% of the radius, whichever is greater) into the tampon or they may be "shallow grooves", primarily surface indentations without significant penetration (of not more than 0.7 mm, not more than 10% of the radius) into the tampon body. Regions between grooves may take the form of ribs.

As used herein the specification and the claims, the term "groove form" and variants thereof relates to a groove or combination of groove segments that are connected in a visibly identifiable manner to provide a unique detached feature at least on the surface of the tampon pledget.

As used herein the specification and the claims, the term "turn" and variants thereof relates to a portion of the groove form in which the groove and/or groove elements reverse(s) upon itself/themselves in a substantially U-shaped or a substantially V-shaped configuration. A "turn" can also have a generally linear extension from the intersection, such as a substantially Y-shaped configuration.

As used herein the specification and the claims, the term "major axis" and variants thereof relating to the groove form is defined by the shortest line connecting the most distant points of the groove form. Generally, this major axis will pass through at least one turn proximate to one end of the pledget.

As used herein the specification and the claims, the term "longitudinal axis" and variants thereof relate to an axis that runs from the insertion end to the withdrawal end substantially through the center of the tampon.

As used in the specification and the claims, the term "self sustaining shape" and variants thereof relate to a tampon pledget that is compressed and/or shaped to assume a general shape and size that is dimensionally stable. For example, a digital tampon that has a self-sustaining shape will generally maintain its shape after a primary package or overwrap is removed and will generally maintain such shape for vaginal insertion. It will be recognized that the tampon is intended to absorb bodily fluids, and may substantially change shape during use as it absorbs such fluids.

As used in the specification and the claims, the term "pledget" and variants thereof relate to a pad or a compress of absorbent material such as fibers designed to absorb bodily fluids.

As used in the specification and the claims, the term "oriented substantially longitudinally" and variants thereof relate to a groove or a groove segment or a groove form that has a helix angle of greater than 45°.

As used in the specification and the claims, the term "fiber density" and variants thereof relate to the relative proportion of fibers to void space in a given volume of the fibrous structure.

The present invention relates to a tampon with reduced opportunity for bodily fluid to flow along the surface without being absorbed into the tampon pledget. This is accomplished by providing at least two detached groove forms each having a generally longitudinal orientation, a length (measured along the groove) that is at least 150% of the length of the pledget, and a turn proximate to at least one of an insertion end and a withdrawal end. The detached groove forms provide visually distinct zones with different bodily fluid handling characteristics. In addition, the turn proximate to at least one end of the tampon provides at least two groove paths for the fluid to follow to be distributed to different portions of the tampon pledget. Thus, not only does the present invention provide tampons with a plurality of grooves, recognized by the prior art as providing improved fluid handling characteristics, but it also provides either fully or partially closed absorption zones that visually communicate functional benefits to the user, including absorbent reservoirs to better contain bodily fluids in the tampon.

Referring to FIG. 1, an intravaginal tampon 10 for feminine hygiene includes a generally cylindrical absorbent pledget 20 and a withdrawal element 30 extending therefrom. The pledget 20 has a longitudinal axis 21, an insertion end 22 (which may terminate in a dome 23), and a withdrawal end 24. The pledget includes a mass of fibers compressed into a self sustaining shape and a sheet-like fluid-permeable cover 25 (such as an apertured film cover) substantially enclosing the mass of fibers. The withdrawal element 30, such as a string, is operatively connected to and extends from the pledget 20 proximate to the withdrawal end 24 thereof.

The pledget 20 includes a plurality of detached groove forms 40 arranged about the outer surface of the pledget 20. In embodiment of FIG. 1, the detached groove forms 40 each comprise a pair of wavy groove segments 41,42 that intersect to create a turn 43 proximate to the insertion end 22 of the pledget 20 and are separate proximate to the withdrawal end 24.

Figure 2:
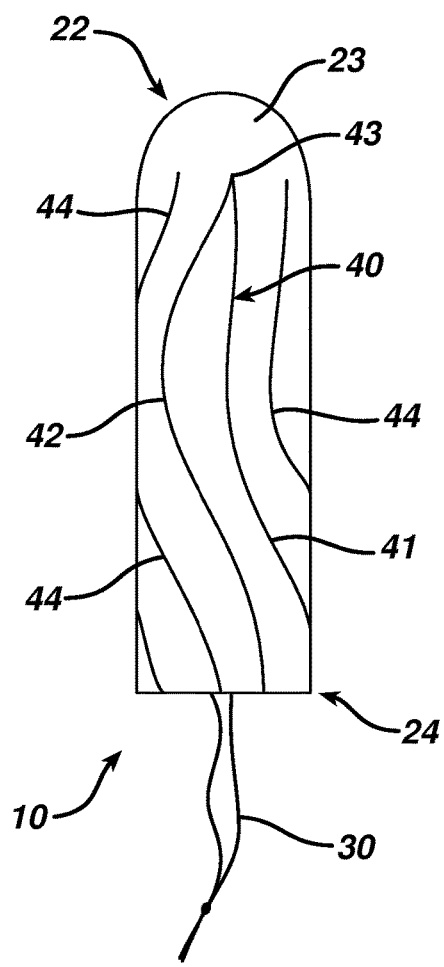
FIG. 2 is a side view of another embodiment of a tampon according to the present invention.

In the embodiment of FIG. 2, additional longitudinal grooves 44 are disposed between detached groove forms 40.

Figure 3:
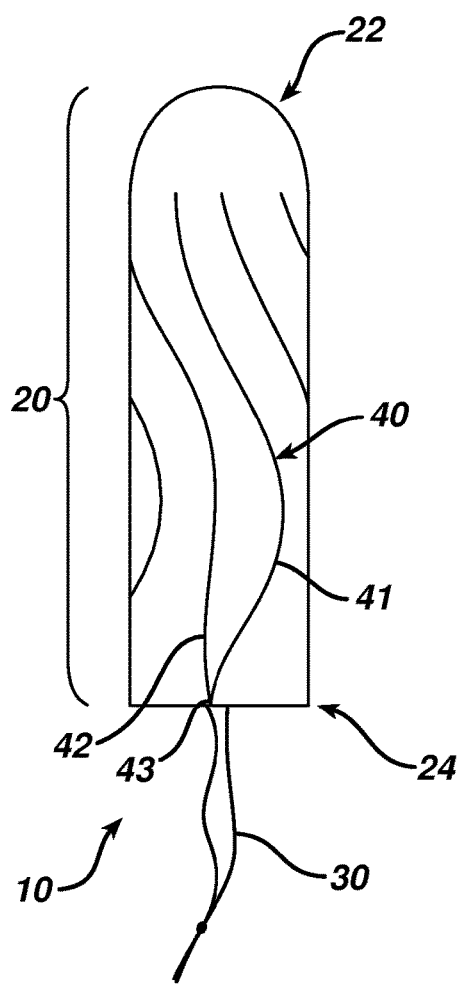
FIG. 3 is a side view of a third embodiment of a tampon according to the present invention.

The embodiment of FIG. 3 is similar to the embodiment of FIG. 1. However, in the embodiment of FIG. 3, the turn 43 is proximate to the withdrawal end 24.

Figure 4:
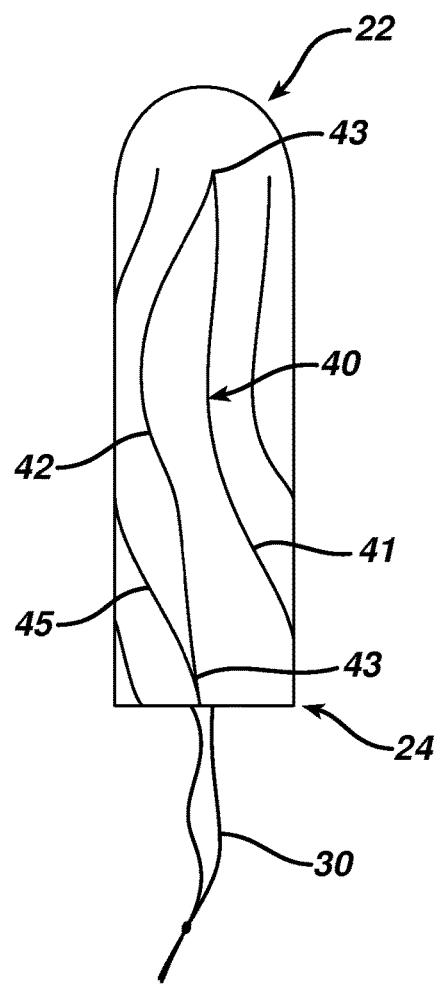
FIG. 4 is a side view of a fourth embodiment of a tampon according to the present invention.

The embodiment of FIG. 4 is similar to the embodiment of FIG. 1. However, in the embodiment of FIG. 4, an additional longitudinal groove segment 45 intersects with groove segment 42 to form a second turn 43 proximate to the withdrawal end 24. This forms a substantially inverted "N-shaped" detached groove form.

In the embodiment of FIG. 5, the detached groove forms 40' each comprise a pair of groove segments 41',42' that intersect to create a turn 43' proximate to both the insertion end 22 and the withdrawal end 24 of the pledget 20 to provide discrete surface zones 46 bounded by the encircling groove forms 40'.

In the embodiment of FIG. 6, additional longitudinal grooves 44 are disposed between detached groove forms 40'.

Again the groove forms may comprise a plurality of groove segments. These groove segments may have a configuration that is a straight line, a plurality of linked angled segments (such as a saw tooth waveform or a square waveform), a plurality of curved segments (such as a sinusoidal waveform), and combinations thereof.

The configuration of the groove segments may differ between groove forms, or they may be the same. The configuration of groove segments within each groove form may also be the same or different. Additional grooves, including longitudinal grooves 44, may be configured similarly to or distinct from each other and the configuration of the groove segments making up the groove forms 40.

The absorbent pledget includes a mass of fibers compressed into a self sustaining shape. The pledget may also include additional absorbent materials such as foam, superabsorbent, hydrogels, and the like. Preferred absorbent material for the present invention includes foam and fiber. Absorbent foams may include hydrophilic foams, foams which are readily wetted by aqueous fluids as well as foams in which the cell walls that form the foam themselves absorb fluid.

Preferably, the fibers employed in the formation of the absorbent body include regenerated cellulosic fiber, natural fibers and synthetic fibers. Preferably, the materials employed in the formation of a tampon according to the present invention include fiber, foam, hydrogels, wood pulp, superabsorbents, and the like. A useful, non-limiting list of useful absorbent body fibers includes natural fibers such as cotton, wood pulp, jute, and the like; and processed fibers such as regenerated cellulose, cellulose nitrate, cellulose acetate, rayon, polyester, polyvinyl alcohol, polyolefin, polyamide, polyacrylonitrile, and the like. Other fibers in addition to the above fibers may be included to add desirable characteristics to the absorbent body. Preferably, tampon fibers are rayon, cotton, or blends thereof, and more preferably, the fibers are rayon. The fibers may have any useful cross-section.

Fiber cross-sections include multi-limbed and non-limbed. Multi-limbed, regenerated cellulosic fibers have been commercially available for a number of years. These fibers are known to possess increased specific absorbency over non-limbed fibers. A commercial example of these fibers is the Galaxy® multilimbed viscose rayon fibers available from Kelheim Fibres GmbH, Kelheim, Germany. These fibers are described in detail in Wilkes et al., U.S. Pat. No. 5,458,835, the disclosure of which is hereby incorporated by reference. Preferably, the fibers include hydrophilic fibers, and more preferably, the fibers include absorbent fibers, i.e., the individual fibers, themselves, absorb fluid. A useful, non-limiting list of useful tampon fibers includes natural fibers such as cotton, wood pulp, jute, hemp, and the like; and processed fibers such as regenerated cellulose, cellulose nitrate, cellulose acetate, rayon, polyester, polyvinyl alcohol, polyolefin, polyamine, polyamide, polyacrylonitrile, and the like. Other fibers in addition to the above fibers may be included to add desirable characteristics to the absorbent body. For example, hydrophobic fibers may be used in outer surfaces of the tampon to reduce surface wetness and hydrophilic fibers may be used to increase the rate of fluid transport into and throughout the body. Preferably, the tampon fibers are rayon or cotton, and more preferably, the fibers are rayon. The fibers may have any useful cross-section.

The pledget includes a mass of fibers substantially enclosed by a sheet-like cover material fluid-permeable cover. Thus, the cover encloses a majority of the outer surface of the tampon. This may be achieved as disclosed in Friese, U.S. Pat. No. 4,816,100, the disclosure of which is herein incorporated by reference. In addition, either or both ends of the tampon may be enclosed by the cover. Of course, for processing or other reasons, some portions of the surface of the tampon may be free of the cover. For example, the insertion end of the tampon and a portion of the cylindrical surface adjacent this end may be exposed, without the cover to allow the tampon to more readily accept fluids.

The cover can ease the insertion of the tampon into the body cavity and can reduce the possibility of fibers being separated from the tampon. Useful covers are known to those of ordinary skill in the art, and they are generally dimensionally stable with low elongation in both the machine and cross-direction. They may be selected from an outer layer of fibers which are fused together (such as by thermobonding), a nonwoven fabric, an apertured film, or the like. Preferably, the cover has a hydrophobic finish.

While liquid permeable covers are beneficial additions to radially-compressed tampons, their dimensional stability can produce some processing challenges. For example, radially compressing a cylindrical tampon blank having a dimensionally stable cover disposed about the cylindrical outer surface can result in cover wrinkles or loose cover extending from the outer surface of the compressed tampon pledget. Therefore, many processes involving radial compression of a tampon blank account for this by folding or tucking the cover material into grooves or folds that penetrate relatively deeply into the absorbent structure.

A process useful in the formation of an intravaginal tampon for feminine hygiene of the present invention with grooved zones begins with an open fibrous structure. The open structure may be a nonwoven fibrous web, a mass of randomly or substantially uniformly oriented fibers and optional materials, such as foams, or particles, and the like. This mass is then manipulated to form a tampon blank.

A nonwoven web useful in the present invention can be formed in any manner desired by the person of ordinary skill in the art. For example, fibers can be opened and/or blended by continuously metering them into a saw-tooth opener. The blended fibers can be transported, e.g., by air through a conduit to a carding station to form a fibrous web. Alternatively, a mass of substantially randomly oriented fibers can be formed by opening and/or blending them, transporting them, as above, to a station to form, e.g., a teabag-type tampon blank. Further processes may employ oriented fibers in a fibrous tow.

The tampon blank can be further processed to form a tampon. In a tampon forming process, a web can be formed into a narrow, fibrous sliver and convolutely wound to form a tampon blank. In addition, a liquid-permeable cover material can be wrapped around the tampon blank to substantially contain the fibrous absorbent portion of the tampon. It may be desired to process the fibrous sliver with selective needle-punching of the sliver as disclosed in U.S. Pat. No. 7,845,055 to Kimball et al., the disclosure of which is herein incorporated by reference.

Figure 7:
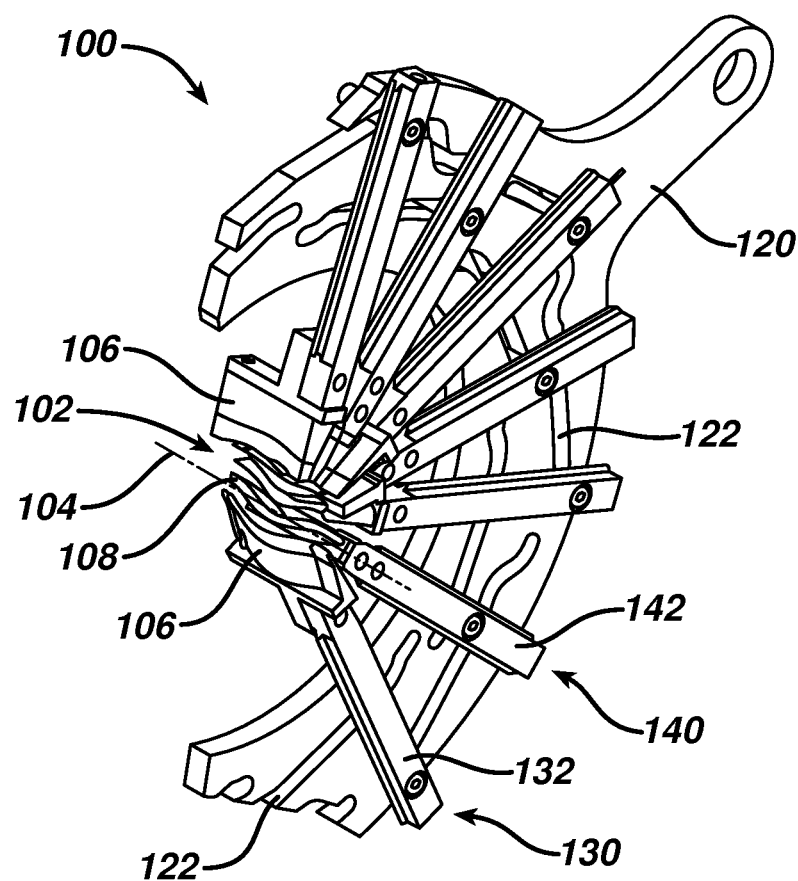
FIG. 7 is a perspective view of a press having a single cam useful in forming tampons of the present invention; the cam is partially broken away, and some of the press elements have been removed for increased clarity of the illustrated press elements.

As shown in FIGS. 7-16, the intravaginal tampon for feminine hygiene of FIG. 1 having a predetermined finished diameter can be formed in a press 100 having (1) a generally cylindrical press cavity 102 having a central press axis 104 and a substantially cylindrical circumference and (2) a plurality of elongate press dies. A partially broken-away perspective view of the press 100 is shown in FIG. 7. This figure includes only seven of sixteen press dies and a portion of the press cam removed for clarity. The press dies may include penetrating dies 106 having pressing faces for defining a set of penetrating grooves that extend into the finished tampon pledget and shaping dies 108 for forming surface features, including shallow grooves on the outer surface of a resulting compressed tampon pledget, or smoothing the outer surface of a resulting compressed tampon pledget, or forming a continuous diameter for guiding resulting compressed tampon pledget out of the press during the ejection step. The penetrating dies 106 and shaping dies 108 alternate about the circumference of the cylindrical press cavity.

Figure 8:
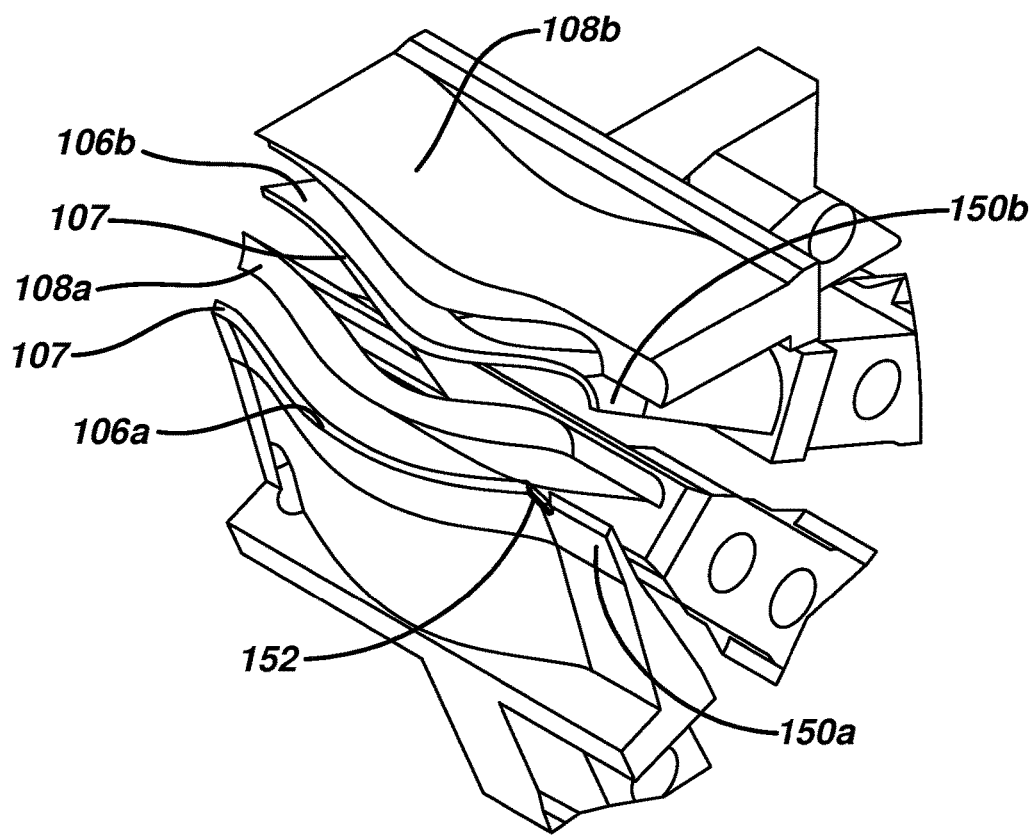
FIG. 8 is perspective view of four of the press dies of the press of FIG. 7.

More detail of the press dies can be seen in FIG. 8, an enlarged view of the bottom right four press dies of FIG. 7. In this view, a first penetrating die 106a has a pressing face 107 and shape corresponding to groove segment 41 and a second penetrating die 106b has a shape corresponding to groove segment 42 (of FIG. 1). As can be seen in FIG. 8, one end 150a of the first penetrating die 106a extends beyond the corresponding end 150b of the second penetrating die 106b. Indeed, the end 150b of the second penetrating die 106b is curved toward the first penetrating die 106a in order to form the turn 43 in the surface of the tampon pledget 20 (as shown in FIG. 1) proximate to the insertion end 22. In this embodiment, the end 150a of the first penetrating die 106a corresponds to the insertion end 22 of the tampon pledget 20 of FIG. 1.

Turn 43 of the detached groove form 40 is formed by the intersection between groove segments 41 and 42 (see FIG. 1). To form a groove form 40, the penetrating dies 106a, 106b travel on a path that crosses during the compression of the tampon blank 200 (see FIG. 9) to form the pledget 20. Therefore, the longer penetrating die 106a has a notch 152 formed (see FIG. 8) proximate to, although spaced from, the end 150a to permit the end 150b of penetrating die 106b to pass across the path of travel of penetrating die 106a.

The shaping dies 108 are shaped to accommodate the shape of the penetrating dies 106 disposed therebetween. Thus, shaping die 108a corresponds to the surface of the pledget 20 contained by the groove segments 41 and 42 and the turn 43. This shaping die 108a is shorter than shaping die 108b corresponds to the surface of the pledget 20 that is open to the insertion end 22.

In the foregoing description, the grouping of the four press pieces may be repeated four times to provide four "petals" around the circumference of the tampon pledget. Alternatively, there could be three sets of the four press dies to form three "petals" around the circumference of the tampon pledget.

Figure 7A:
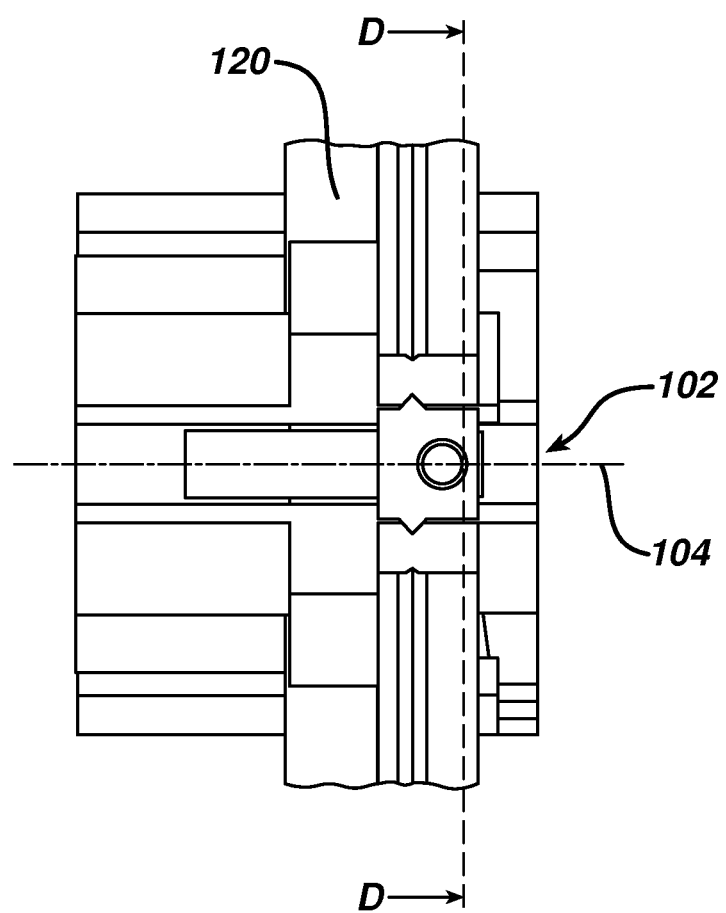
FIG. 7A is a side view of the central portion of the press of FIG. 7 including the press dies and central cavity; outer portions of the cam and other press elements are broken away for increased clarity of the central press portion.
Figure 9:
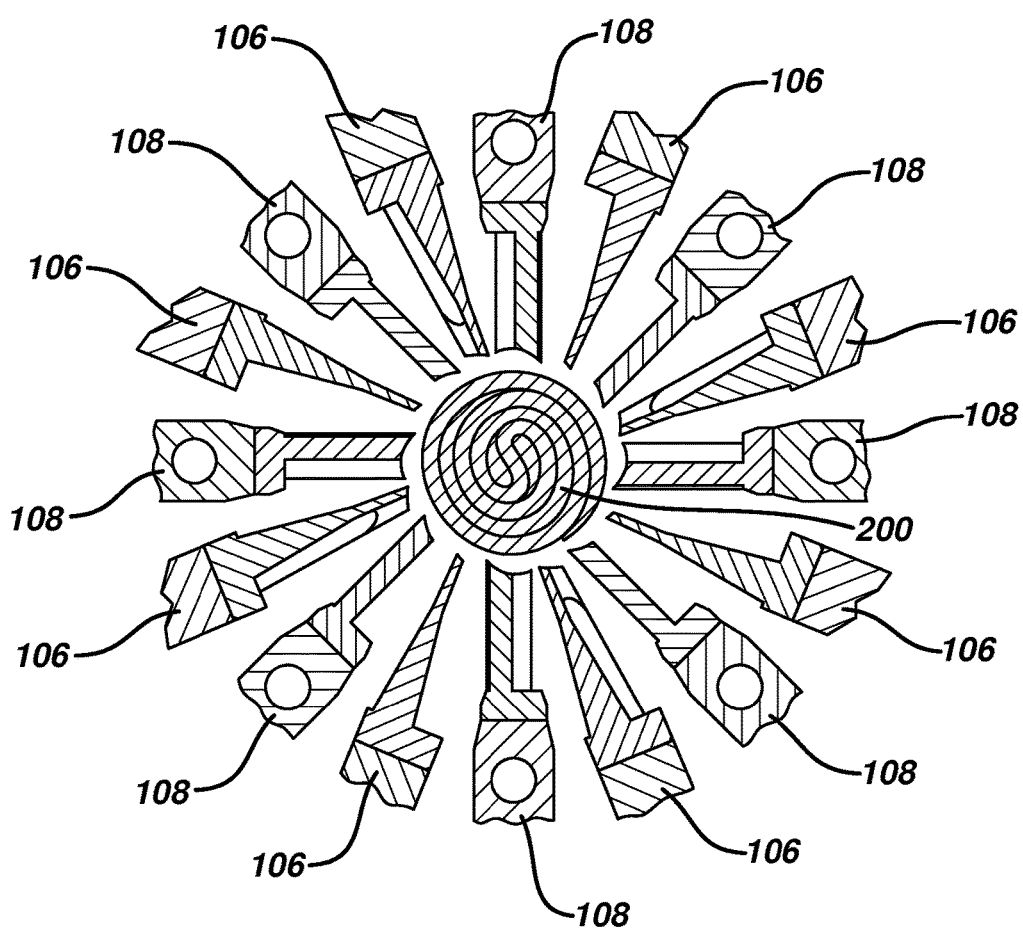
FIG. 9 is cross-section of the central portion of the press of FIG. 7A along line (D-D) in an open position; outer portions of the press elements are broken away for increased clarity of the central press portion.
Figure 10:
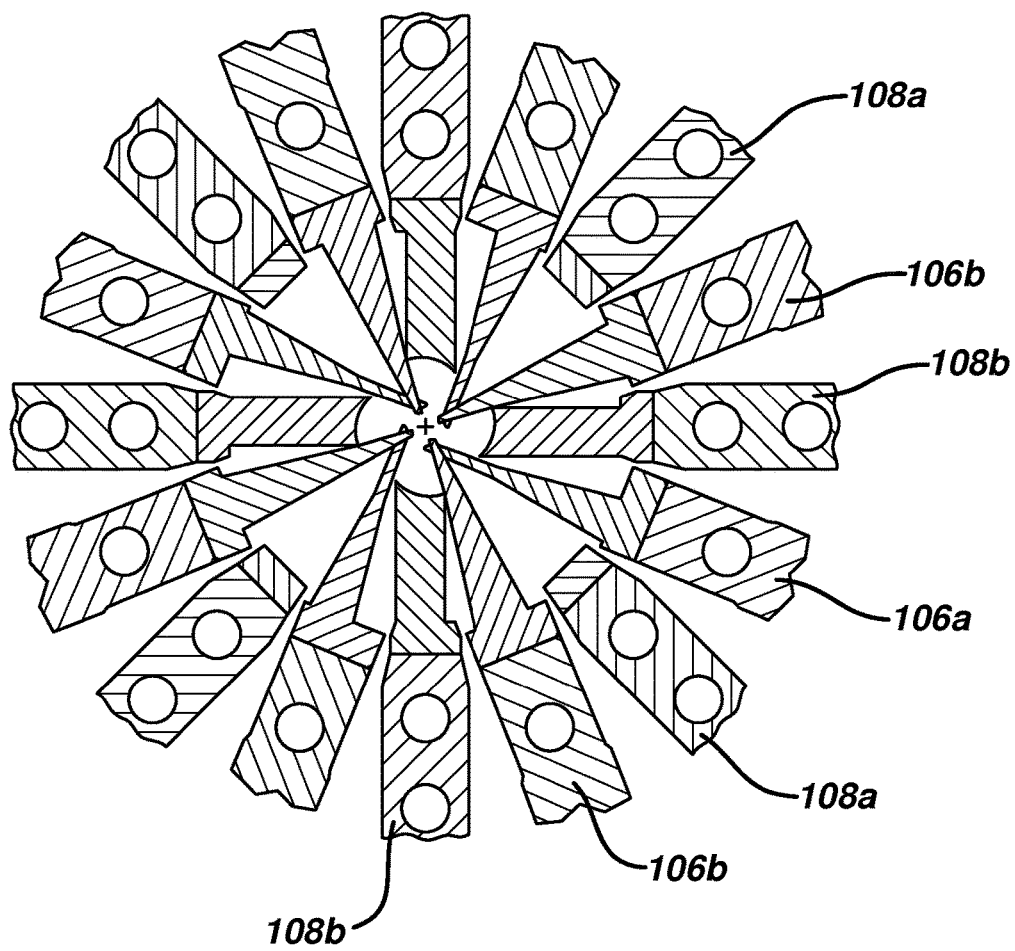
FIG. 10 is a cross-section of the central portion of the press of FIG. 7 proximate the notch during an initial compression step; outer portions of the press elements are broken away for increased clarity of the central press portion.
Figure 11:
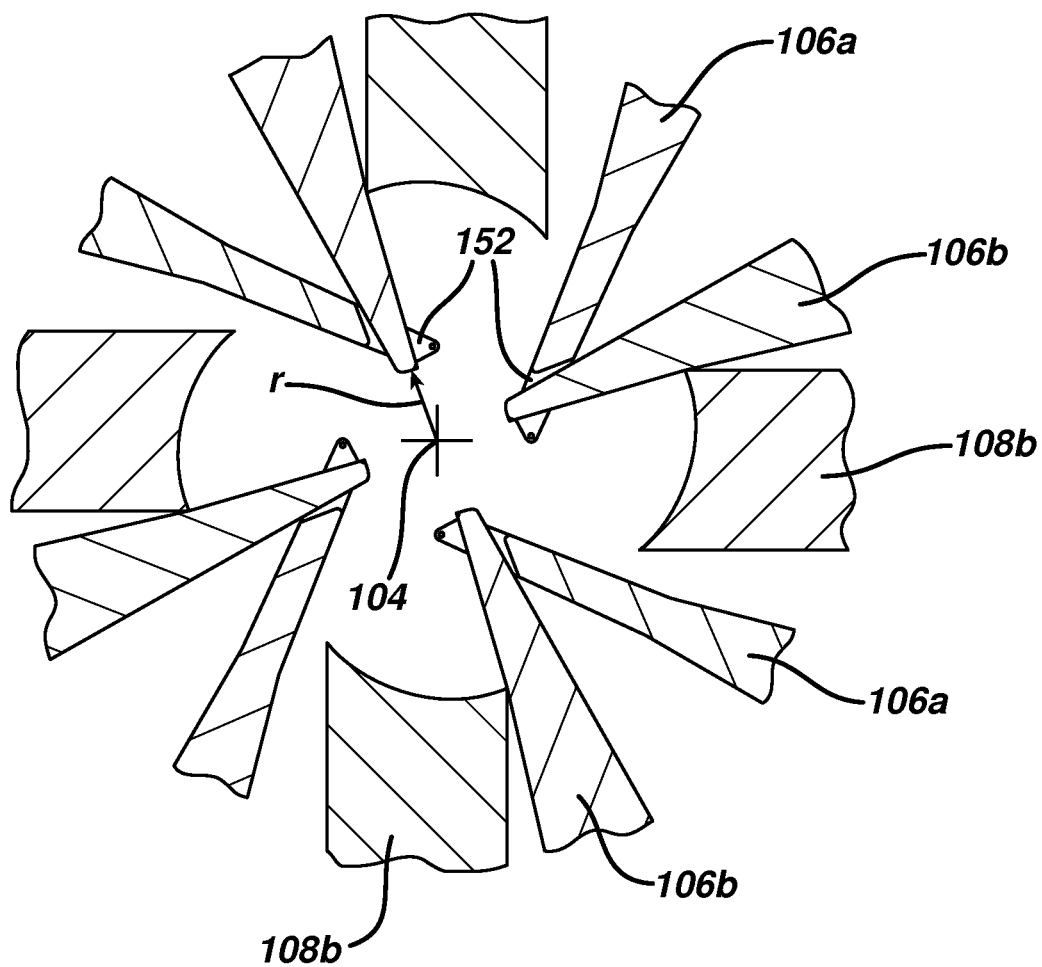
FIG. 11 is an enlarged cross-section view of the press of FIG. 10 clearly showing the penetrating die tips crossing during an initial compression step; the remaining press elements are broken away.
Figure 12:
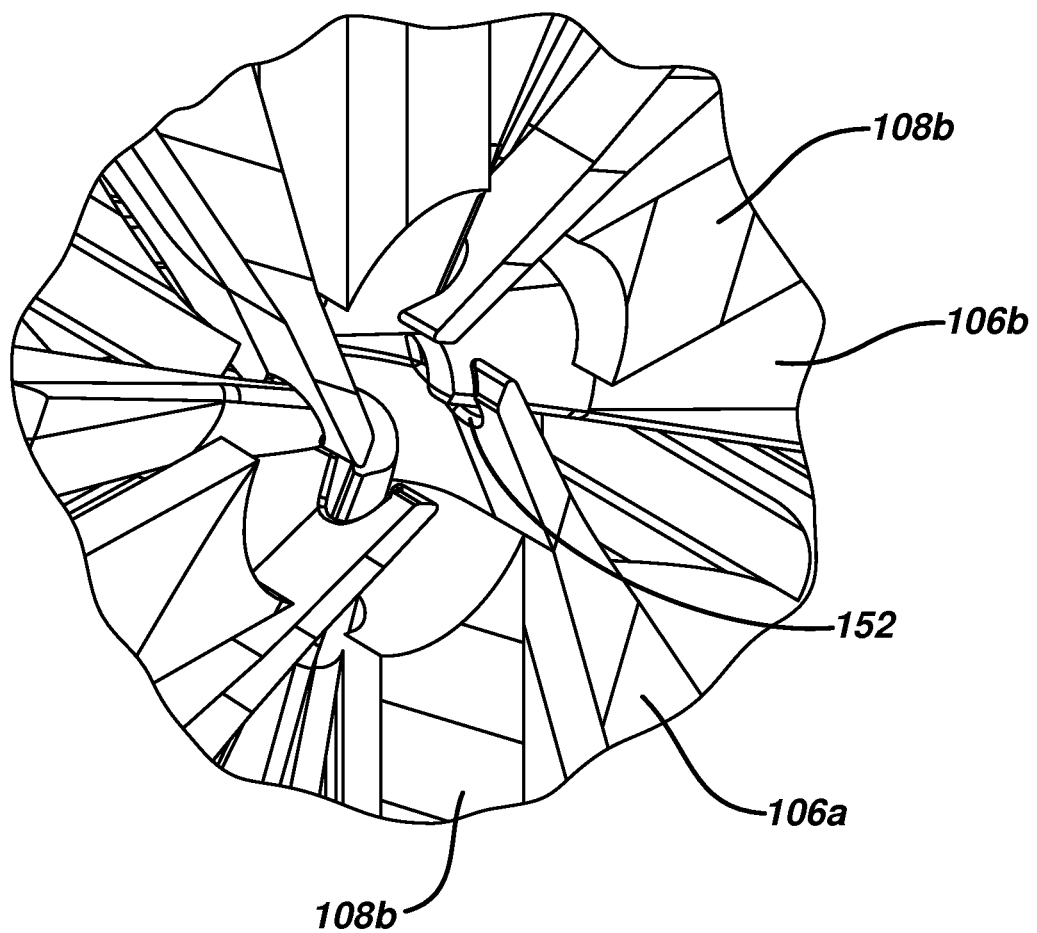
FIG. 12 is an enlarged perspective view of the press of FIG. 11; the remaining press elements are broken away.

In this process, a substantially cylindrical tampon blank 200 is inserted into the press cavity 102 in an open position shown in FIG. 9 (a cross-section of the press of FIG. 7A and tampon proximate to the notch 152 in the first penetrating die 106a, looking from the interior of the press toward the end of the press corresponding to the insertion end of the tampon in FIG. 1), after which an initial compression step is performed. In this initial compression step, at least the penetrating dies 106 are moved into the press cavity 102 to a penetrating die closed position having a clear distance "r" (see FIG. 11) from the press axis 104 that is less than the predetermined finished diameter as shown in FIG. 10 and in detail in FIGS. 11 and 12. This causes portions of adjacent penetrating dies that form the turn to pass through the same space within the press. As shown in FIG. 12, this can be accomplished by forming a notch 152 in the first penetrating dies 106a to permit the second penetrating dies 106b to cross therethrough in the penetrating die closed position. This initial compression step forms the compressed fibrous core of the tampon and provides column strength for easy insertion without need for a tampon applicator, known in the art as digital insertion.

Figure 13:
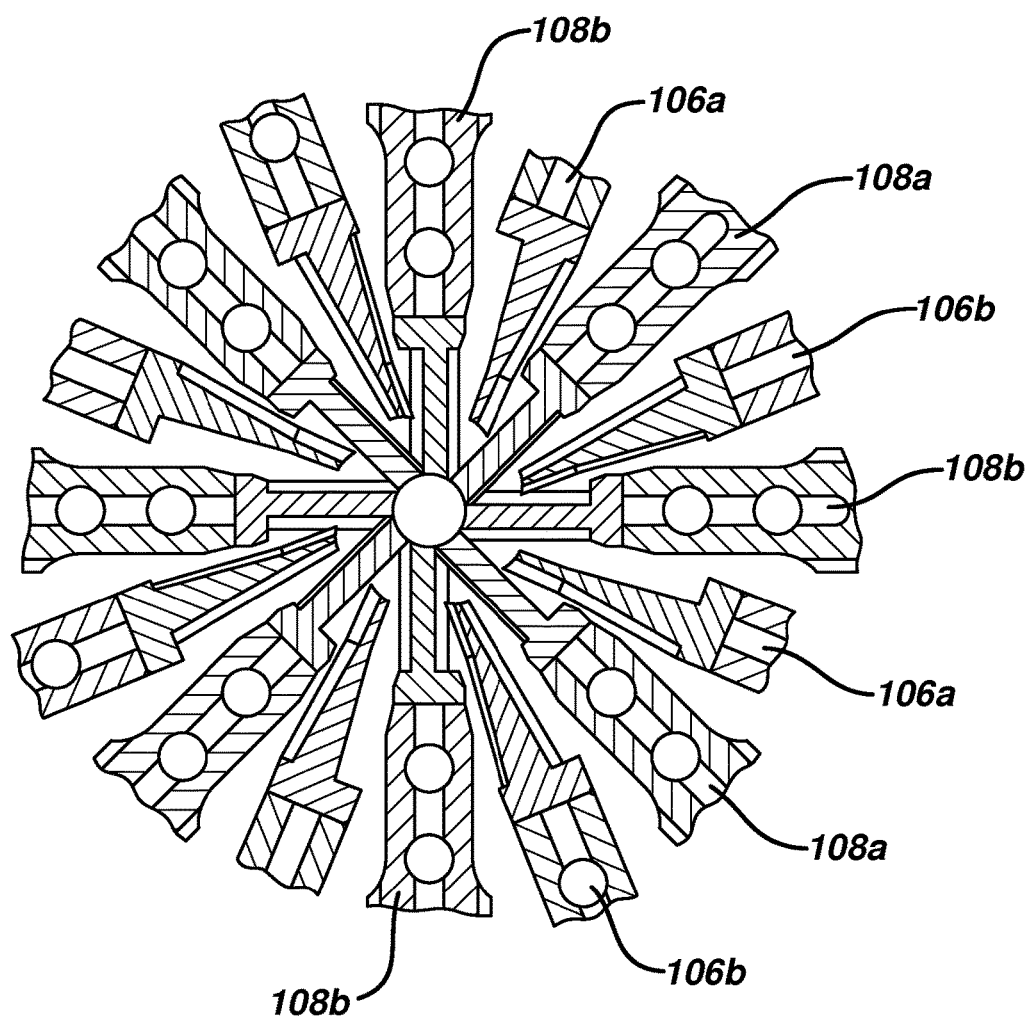
FIG. 13 is cross-section view of the central portion of the press of FIG. 7A along line (D-D) during an ejection step; outer portions of the press elements are broken away for increased clarity of the central press portion.
Figure 14:
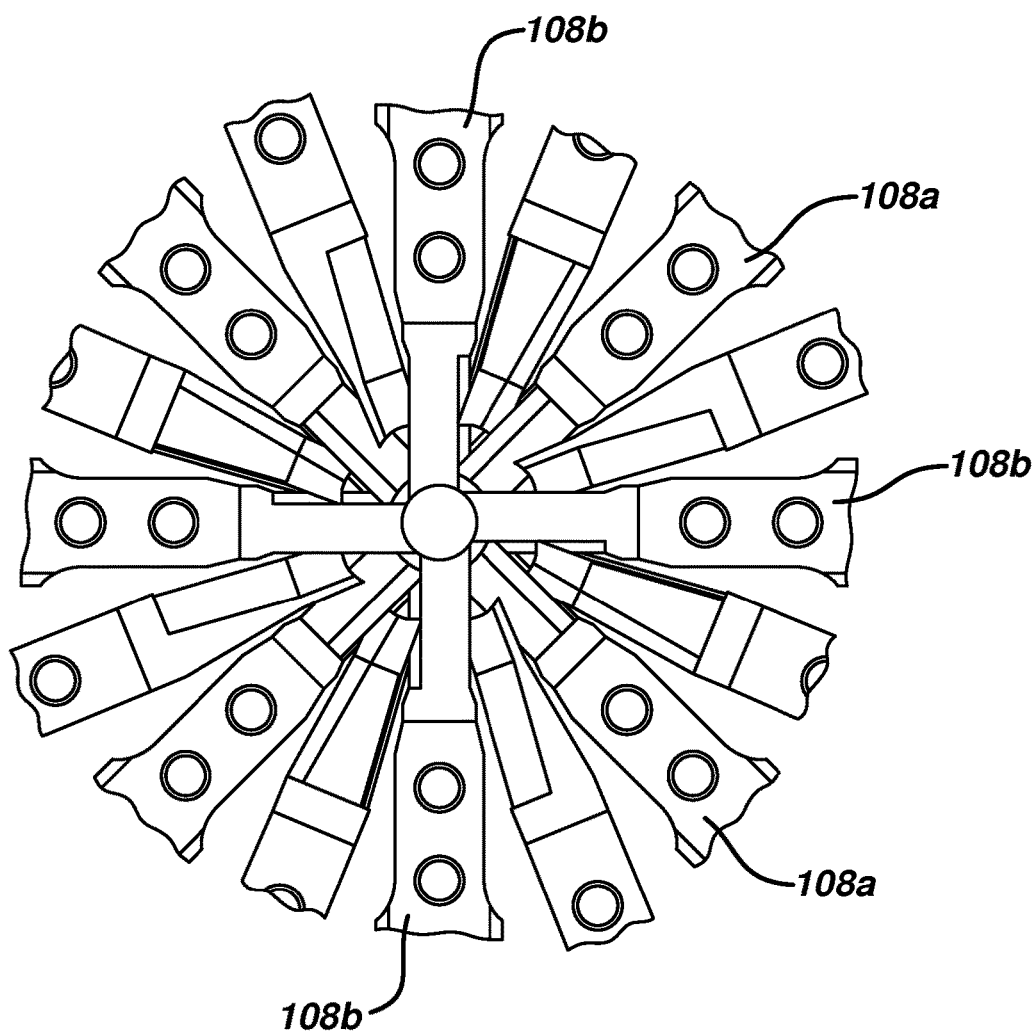
FIG. 14 is an end view of the press of FIG. 13 in the ejection position.
Figure 15:
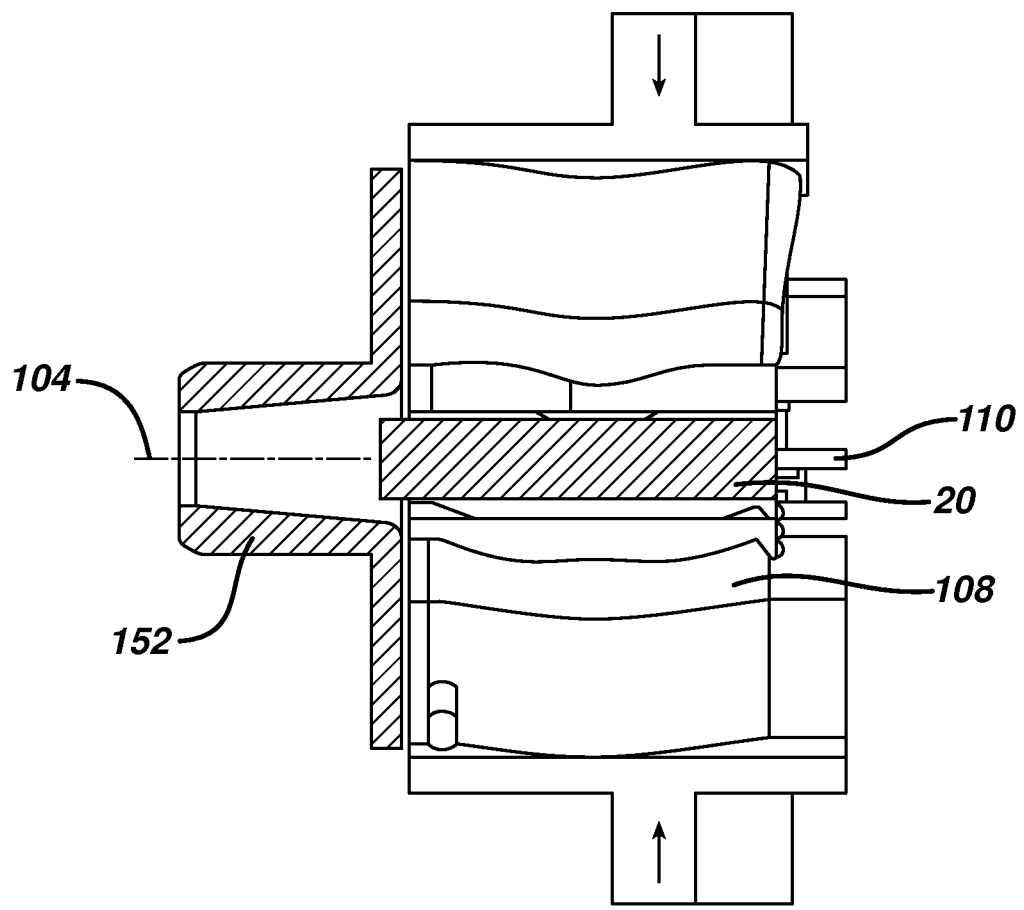
FIG. 15 is a longitudinal cross-section of the press of FIG. 13, during an ejection step.

In one embodiment, a second compression step that applies to the substantially longitudinal ribs of the preform a radial pressure directed toward the central press axis to provide a compressed tampon pledget of reduced diameter relative to the preform is represented in FIGS. 13 (a cross-section of the press, proximate to the center of the press cavity) and 14 (an end view of the press). In this step, the penetrating dies 106 are retracted to assume a clear distance from the press axis that is sufficient to permit the shaping dies 108 to advance toward the press axis beyond the penetrating dies. Then the set of shaping dies is moved to a shaping die closed position. The compressed tampon pledget may be ejected from the press cavity 102 using the shaping dies 108 to provide a substantially smooth guide for the compressed tampon pledget to permit removal of the compressed tampon pledget from the press and pushing on one end of the compressed tampon pledget with a push rod 110 (shown in FIG. 15).

The tampon can be further shaped and packaged. For example, the insertion end can be formed into a hemispherical or elliptical dome shape, and the tampon can be enclosed in a primary packaging material that can also support the final shape of the tampon.

In somewhat greater detail, the tampon press 100 of FIGS. 7 and 8 includes a cam 120, penetrating die assemblies 130, and shaping die assemblies 140. The cam 120 is generally circular and includes slots 122 to urge the die assemblies 130, 140 into and out of the press cavity 102 as the cam is pivoted about the press axis 104. Each penetrating die assembly 130 includes a pair of slides (an exemplary slide 132 is shown on one side of the cam 120; another, not shown, would be on the opposite side of the cam 120) and the penetrating die 106. Each shaping die assembly 140 includes a pair of slides (an exemplary slide 142 is shown on one side of the cam 120; another, not shown, would be on the opposite side of the cam 120) and the shaping die 108. Alternatively, multiple cams 120a, 120b may be used to permit more variability to the control of the movement of the dies, e.g., one cam could operate penetrating dies 106 and another could operate shaping dies.

Figure 16:
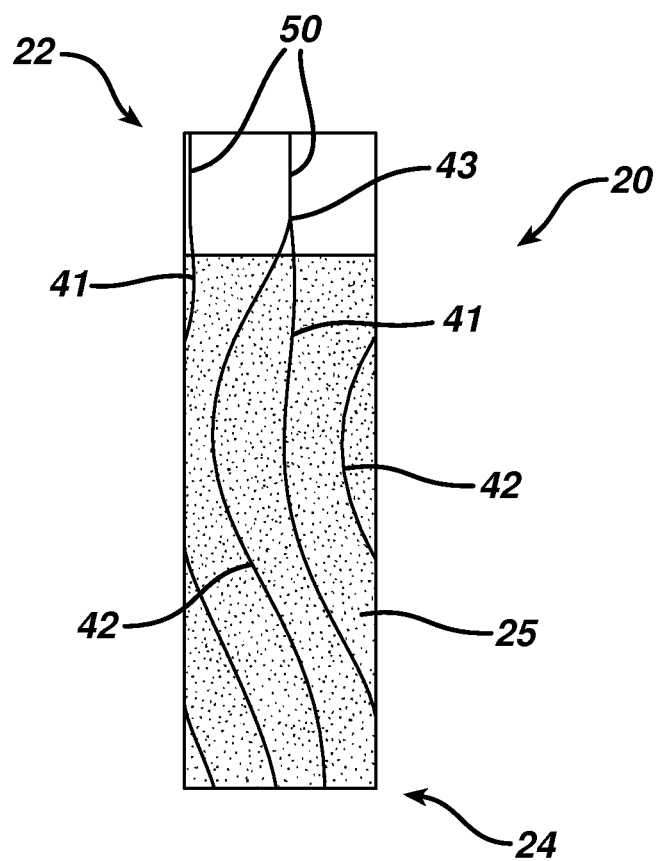
FIG. 16 is a side elevation of a compressed tampon pledget prior to finishing the insertion end and packaging.

Upon ejection from the press 100, compressed pledget 20 is generally cylindrical as shown in FIG. 16. The pressed groove segments generally extend from the insertion end 22 to the withdrawal end 24. Those pressed groove segments 50 that extend from the turn 43 to the insertion end 22 of the pledget will essentially be restructured in the doming process mentioned above to substantially eliminate them, both aesthetically and functionally. This is enhanced by the absence of the cover 25 in the region of the dome 23.

In an alternative embodiment, especially enabled by a multiple cam controlled process, the penetrating jaws 106a, 106b may be controlled to advance them separately. For example, penetrating jaw 106b may be advanced to the closed position, withdrawn sufficiently to permit penetrating jaw 106a to fully advance toward the press axis 104 in the closed position. This eliminates the need for notch 152 in penetrating jaw 106a, as the two penetrating jaws do not need to occupy the same space at the same time. In addition, as described in the embodiment, below, this could permit penetrating jaws 106a to remain in contact with the compressed tampon pledget 20 during ejection from the press.

Figure 17:
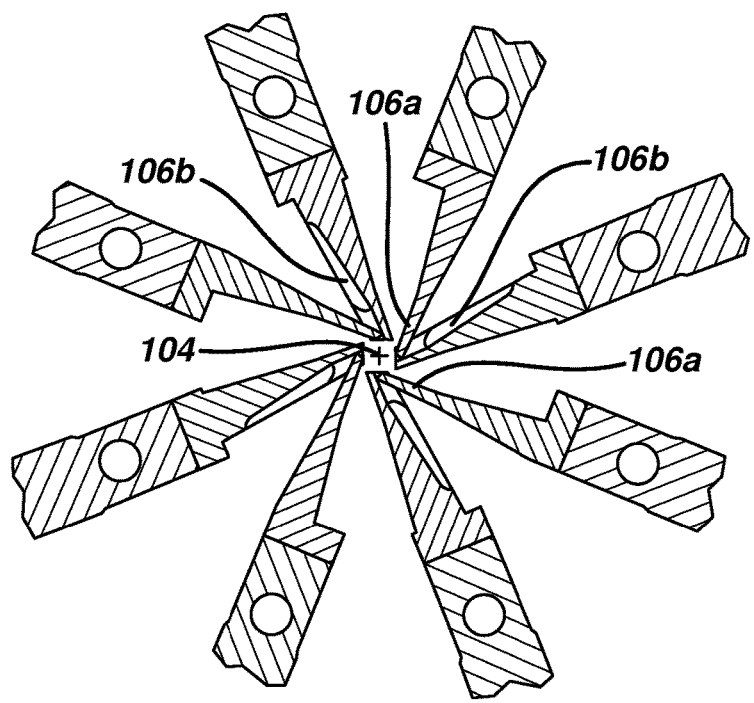
FIG. 17 is cross-section view of the central portion of an alternative press during an initial compression step.
Figure 18:
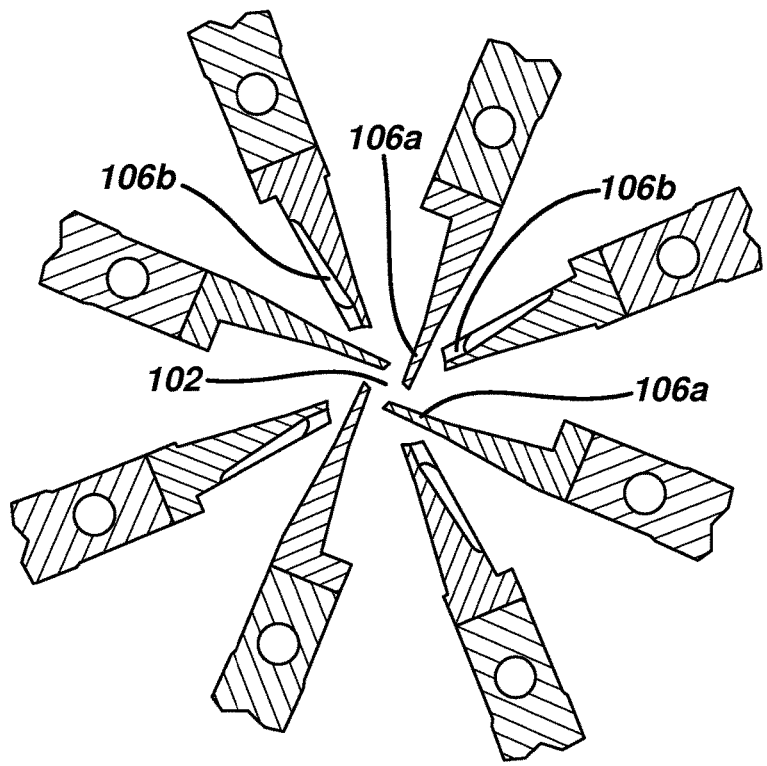
FIG. 18 is cross-section view of the press of FIG. 17 during an ejection step showing penetrating dies capable of guiding the compressed tampon pledget from the press cavity.

In an alternative process, shown in FIGS. 17-18, the shaping dies 108 may be eliminated. Again, a substantially cylindrical tampon blank 200 is inserted into the press cavity 102 in an open position (similar to that shown in FIG. 9), after which an initial compression step is performed. In this initial compression step, at least the one set of penetrating dies 106b are moved into the press cavity 102 to a penetrating die closed position having a clear distance from the press axis 104 of less than a final compressed radius of the compressed tampon pledget as shown in FIG. 17. The first set of penetrating dies 106b are withdrawn sufficiently to permit penetrating jaw 106a to fully advance toward the press axis 104 in the closed position. The penetrating jaws 106a may remain in contact with the compressed tampon pledget 20 during ejection from the press. This compression forms the densified fibrous core of the tampon and provides column strength for easy insertion without need for a tampon applicator, known in the art as digital insertion. The compressed tampon pledget is ejected from the press cavity 102 into a reducing bushing to transfer the compressed pledget into a hollow mandrel by pushing on one end of the compressed tampon pledget with a push rod 110 (similar to that shown in FIG. 15).

Figure 19:
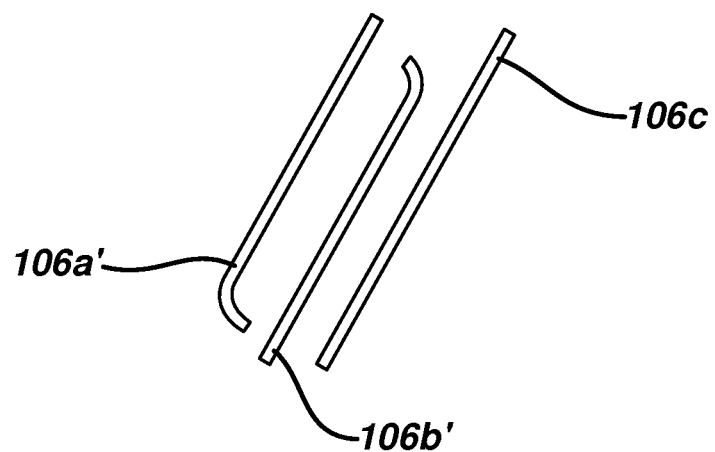
FIG. 19 is a line view of the pressing faces of three penetrating dies useful to form the tampon of FIG. 6.

While the foregoing detailed embodiments describe tampons having four groove forms resulting from eight intersecting groove segments, it will be recognized that the number of groove forms and/or groove segments can be varied, as desired. There may be an even or odd number of groove forms and/or groove segments—for example, embodiments similar to that shown in FIG. 6 could have three or four groove forms separated by an equal number of additional grooves. Thus, a three groove form structure with three additional grooves could be formed with a combination of six intersecting groove segments (forming the three groove forms) and three additional grooves; a total of nine groove segments and/or grooves. A corresponding number of penetrating dies would be required in contrast with the sixteen penetrating dies described in reference to FIGS. 7-16, above. A line drawing of the pressing faces 107 of a set of three adjacent penetrating dies for such an embodiment is shown in FIG. 19. In this drawing, penetrating dies 106a', 106b' create the groove form, while independent penetrating die 106c forms the additional groove 44 between groove forms 40' of FIG. 6.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. Apparatus for manufacturing an intravaginal tampon for feminine hygiene comprising:
   a. a tampon press having a central press axis comprising:
      i. a plurality of elongate press dies disposed about the central press axis to form a press cavity, the elongate press dies comprising a plurality of longitudinal penetrating dies having pressing faces corresponding to a plurality of longitudinal groove segments in a desired compressed tampon pledget and including at least one first penetrating die having a pressing shape corresponding to a desired first groove segment shape and at least one second penetrating die having a pressing face corresponding to a second groove segment shape, wherein the first groove segment shape and the second groove segment shape combine to form a groove form on a tampon formed in the press, the pressing face of the first penetrating die extends longitudinally beyond the pressing face of the second penetrating die toward an end of the press cavity whereby the first and second penetrating die are capable of passing through the same space within the press to form the groove form;
      ii. a control mechanism to control movement of the elongate press dies into and out of the press cavity
   b. a cylindrical carrier having a diameter less than that of the predetermined finished diameter
   c. means to enclose the compressed tampon pledget in a primary package having an internal diameter substantially equal to the predetermined finished diameter.

2. Apparatus of claim 1, wherein the plurality of longitudinal penetrating dies comprises at least two pairs of the first and second penetrating dies.

3. Apparatus of claim 2, wherein the plurality of longitudinal penetrating dies further comprise an independent penetrating die between adjacent pairs of first and second penetrating dies.

4. Apparatus of claim 3, wherein the plurality of elongate dies further comprises a plurality of shaping dies alternating with the penetrating dies arranged and configured to accommodate the penetrating dies and which shaping dies are moveable to a closed position to provide a generally cylindrical press cavity to provide a substantially smooth guide for ejecting the compressed tampon pledget from the press.

5. Apparatus of claim 1, further comprising a forming die having an exit orifice diameter less than the predetermined finished diameter, the forming die disposed coaxial with the press cavity and adjacent an ejection opening in the press.

6. Apparatus of claim 1 further comprising means to finish one end of the compressed tampon pledget.

7. The apparatus of claim 1, wherein the first and second penetrating die are arranged and configured to move simultaneously within the press and the first penetrating die comprises a notch to permit the second penetrating die to pass through the same space within the press to form the groove form.

8. The apparatus of claim 1, wherein the first and second penetrating dies are arranged and configured to move sequentially within the press and the second penetrating die moves into and withdraws from its position of maximum penetration within the press prior to the first penetrating die moving into its position of maximum penetration within the press.

* * * * *